United States Patent [19]

Thomas

[11] 4,092,848

[45] June 6, 1978

[54] METHOD AND APPARATUS FOR DETERMINING HYDROCYCLONE INTERIOR WEAR

[75] Inventor: David Charles Thomas, Oklahoma City, Okla.

[73] Assignee: Kerr-McGee Chemical Corporation, Oklahoma City, Okla.

[21] Appl. No.: 794,213

[22] Filed: May 5, 1977

[51] Int. Cl.² ............................................. G01N 17/00
[52] U.S. Cl. ..................................... 73/86; 33/174 E
[58] Field of Search ............................. 73/86, 432 PS; 33/174 E, 178 R, 168 R

[56] References Cited

U.S. PATENT DOCUMENTS

| | | | |
|---|---|---|---|
| 1,469,343 | 10/1923 | Strong | 33/174 E |
| 3,829,977 | 8/1974 | Lambert | 33/174 E |

*Primary Examiner*—Donald O. Woodiel
*Attorney, Agent, or Firm*—William G. Addison

[57] ABSTRACT

This invention relates to a method and apparatus for readily determining the wear experienced in the interior conical section of a hydrocyclone during use of the hydrocyclone.

In the practice of this invention, the apparatus is inserted into the hydrocyclone interior until it is flush with the conical interior section of the hydrocyclone after which the length of the tip of the apparatus protruding from the hydrocyclone is measured. As the conical interior section of the hydrocyclone wears during use, the length of the protruding tip of the apparatus will increase upon measurement. A rejection criteria is developed based on independent measurements while maintaining the desired particle size distribution in the overflow product and the desired flow split ratio of overflow to underflow of the fluid hydrocyclone feed material to determine at what point a hydrocyclone should be rejected as no longer suitable to achieve the desired hydrocyclone separation while maintaining the desired flow split ratio.

4 Claims, 7 Drawing Figures

METHOD AND APPARATUS FOR DETERMINING HYDROCYCLONE INTERIOR WEAR

BACKGROUND OF THE INVENTION

1. Field of the Invention

This invention relates to a method and apparatus for readily determining the wear experienced in the conical interior section of a hydrocyclone during use.

This invention further relates to a method and apparatus for readily determining the wear experienced in fluid nozzles, venturis or other orifices subject to wear that are too small to allow for conventional wear measurements.

2. Description of the Prior Art

To the knowledge of this invention, there are no known equivalents to this invention. However, no extensive search of the prior art has been conducted by this inventor.

DESCRIPTION OF THE PREFERRED EMBODIMENTS

Figure 1:
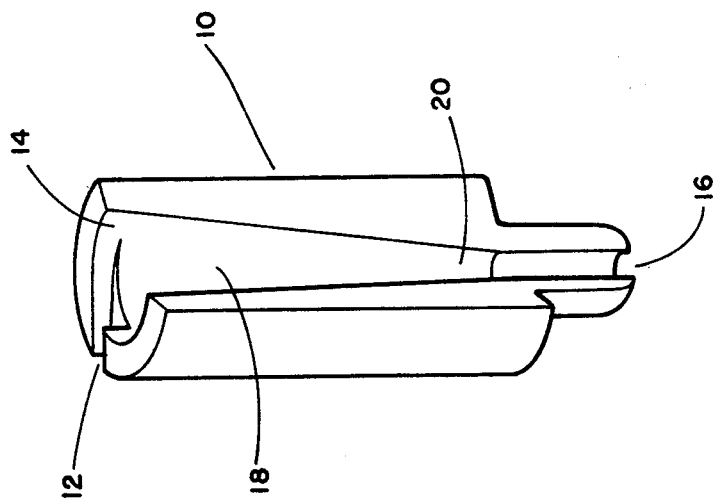
FIG. 1 provides a schematic illustration of a typical hydrocyclone.

Turning now to FIG. 1, the principle features of a hydrocyclone are schematically illustrated. General reference numeral 10 provides a typical hydrocyclone having an inlet 12, an overflow outlet 14 and an underflow outlet 16. A fluid feed material enters the inlet 12 under pressure thus producing a high velocity flow. Inlet 12 is designed such that it contacts a conical interior section 18 of hydrocyclone 10 in a tangential manner to the axis of the hydrocyclone and with a slightly downward pitch. The entering fluid feed material thus travels vertically downward along a spiral path and as a result of the high velocity of flow produces a strong centrifugal gravity field that forces larger more dense particles contained within the feed material to be separated and removed to the outer wall of conical section 18.

Figure 2:
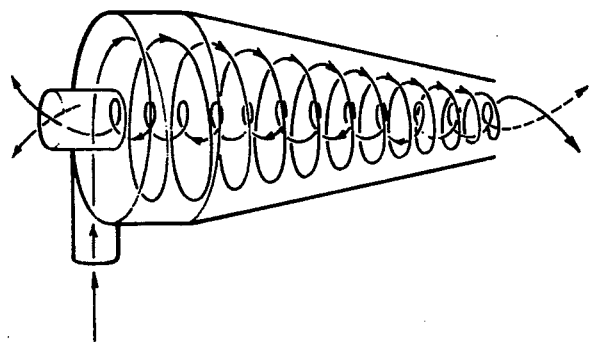
FIG. 2 provides a diagrammatic illustration of the flow path exhibited by a fluid passing through a hydrocyclone.

The underflow outlet 16 is too small to allow all the feed material to exit, therefore, a flow reversal occurs in conical section 18 that returns a portion of the feed material to the overflow outlet 14 while the separated larger, more dense particles contained in the feed material exit by outlet 16. This flow pattern is diagrammatically illustrated in FIG. 2. Further, it must be noted that the application of underflow back pressure to underflow outlet 16 will also effect the amount of material which is caused to exit by overflow outlet 14 and thereby effect the amount of larger, more dense particles which exit by overflow outlet 14 with the feed material.

The purpose of underflow back pressure is to provide a means of controlling the hydrocyclone flow split ratio of overflow to underflow. Technically, any restriction of the underflow outlet 16 will cause an increase in the overflow to underflow ratio of a particular hydrocyclone. However, it has been found that modest underflow restrictions do not substantially effect the flow split ratio but do allow a reasonable amount of control over the flow split ratio. More importantly, it has been found that excessive underflow restriction can cause an unstable flow condition which can cause the hydrocyclone to plug. Thus, only modest underflow restriction is preferred.

It must also be emphasized that the flow reversal which occurs is in the direction of vertical flow, not in the direction of rotational flow of the fluid feed material. This vertical flow reversal thereby produces a zone 20 contained within conical section 18 and located in the lower third of the hydrocyclone wherein the vertical velocity of the fluid is zero. If a feed material particle of exactly the same density as the fluid were to become trapped in this location, as for example, as a result of the application of underflow back pressure to underflow outlet 16, the particle might spin around the axis of the hydrocyclone indefinitely thus causing erosional wear of the interior of the hydrocyclone.

The basic problem of achieving satisfactory hydrocyclone separations has been discovered to be an interaction of hydrocyclone conical interior wear and underflow back pressure.

Hydrocyclone wear, concentrated in the lower third as in zone 20 within conical section 18 of the hydrocyclone can take the form of spiral grooves, rings, or simply an increase in the diameter of the underflow outlet 16 caused by gradual erosion. The spiral grooves are caused by large particles in the feed material following a preferential path downward through the hydrocyclone. The ring-shaped wear patterns are caused by either complete blockage of the underflow outlet 16 or by a back pressure/flow equilization that balances the particles against the outer wall of conical section 18. Since the rotational velocities of the particles against the outer wall of conical section 18 increase as the particles approach the underflow outlet 16, wear is concentrated there.

The effects of interior wear on the hydrocyclone are to: (1) decrease the flow to the overflow outlet 14; (2) increase the flow to underflow outlet 16; and (3) increase the total flow through the hydrocyclone. The net result being a reduction in the percentage of flow exiting as overflow. Since any commercial hydrocyclone operation must maintain a constant throughput of overflow, a method of adjusting the flow split ratio is required. The method used is to apply a restriction of positive underflow back pressure as previously described.

The disadvantage of this procedure is that it results in less of the larger, more dense, particles contained in the feed from being successfully separated and removed from the feed material through underflow outlet 16 thus defeating the normal purpose of a hydrocyclone to separate larger particles from smaller particles and thus enable a controlled size distribution in the overflow product. Further, this procedure results in an increase in turbulence in the lower portion of the hydrocyclone which can accelerate wear. Also, wear is self-accelerating because surface roughness causes turbulence which accelerates wear, and wear requires increased underflow back pressure to maintain the flow split ratio constant which causes more turbulence and more wear.

Figure 6:
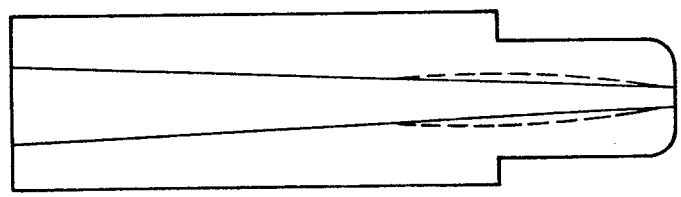
FIGS. 3-6 provide examples of the various wear patterns experienced in a hydrocyclone.
Figure 5:
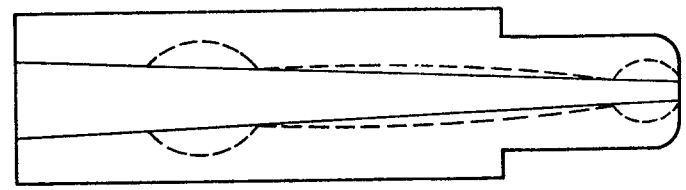
Figure 4:
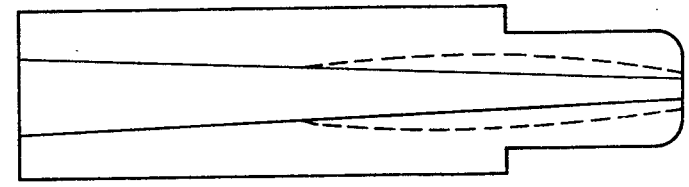
Figure 3:
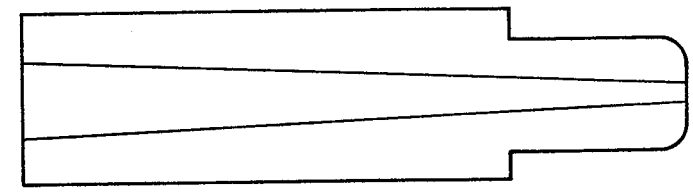

Typical hydrocyclone interior wear patterns are diagrammatically illustrated in FIGS. 3-6. FIG. 3 is a cross section of a new hydrocyclone. FIG. 4 is a cross section of a hydrocyclone with an enlarged underflow outlet as a result of wear. FIG. 5 is a cross section showing heavy ring wear that is indicative of plugged operation or pressure balanced operation, as previously described. FIG. 6 is a cross section showing heavy interior wear of the conical interior without significant enlargement of the underflow outlet.

Thus, it would be desirous to possess an apparatus capable of determining the extent of interior conical section wear of a hydrocyclone to enable a user to determine when a particular hydrocyclone will no longer achieve the desired particle size separation while maintaining the desired flow split ratio.

Figure 7:
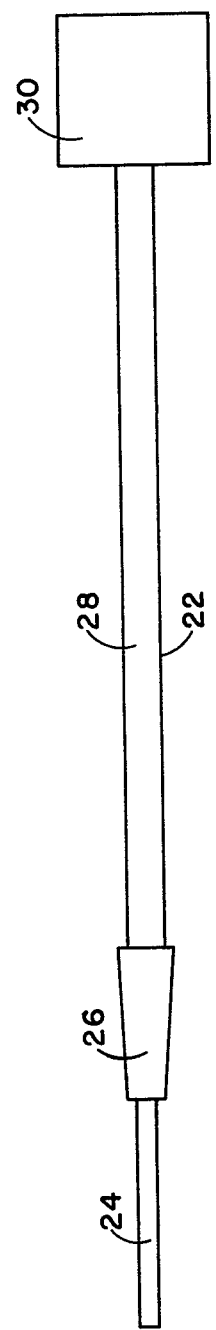
FIG. 7 provides a diagrammatic illustration of one form of apparatus suitable for the practice of this invention.

Turning now to FIG. 7, this invention provides such an apparatus in general reference 22 and a method for using the same to readily determine the wear experienced in the interior conical section of a hydrocyclone.

The apparatus described by general reference 22 is comprised of four sections. The first section comprises a cylindrical section 24 which is smaller in diameter than the diameter of the hydrocyclone underflow outlet 16 of general hydrocyclone reference 10 (FIG. 1). The second section comprises a truncated conical section 26 attached to cylindrical section 24 and possesses a conical taper of angle equal to the angle of the conical interior section 18 of general hydrocyclone reference 10. Truncated conical section 26 is of such a diameter that it would contact the outer wall of conical section 18 within the region designated as zone 20 contained in conical section 18 of general hydrocyclone reference 10.

The third section comprises a cylindrical section 28 which is smaller in diameter than the largest diameter of conical section 26 and of such a length that from the point of attachment with truncated conical section 26 the distance is greater than the distance from zone 20 contained within conical section 18 to the exterior of the overflow outlet 14 of general hydrocyclone reference 10.

The fourth section comprises a handle 30 and may be of any size such as to aid in the handling of the first three sections of the device to which it is attached.

In the practice of this invention, the apparatus is inserted into the hydrocyclone interior from the end of the overflow outlet 14 until it is in flush contact with the conical interior section of the hydrocyclone after which the length of the tip of the apparatus protruding from the underflow outlet 16 of the hydrocyclone is measured. As the conical interior section 18 of the hydrocyclone wears, the length of the protruding tip of the apparatus will increase. A rejection criteria for a particular hydrocyclone is developed based on independent measurements by the device during the use of the hydrocyclone while maintaining the desired particle size distribution in the overflow product and the flow split ratio of the overflow to underflow of the fluid hydrocyclone feed material.

While this invention has been described only as it relates to the determination of the extent of wear experienced in the interior conical section of a hydrocyclone, it is to be understood that the subject of this invention is equally applicable to fluid nozzles, venturis or other orifices which are subject to wear and is intended to be limited only by the following claims.

What is claimed is:

1. An apparatus adapted for insertion in a hydrocyclone provided with an inlet, underflow outlet and overflow outlet for determining the extent of wear of the interior conical section of said hydrocyclone comprising:
    (1) a first section comprising a cylindrical section of a diameter less than the diameter of the underflow outlet of the hydrocyclone;
    (2) a second section connected to the first section comprising a truncated conical section possessing an angle of taper equal to the angle of the interior conical section of the hydrocyclone and of such a diameter as to contact the lower section of the interior conical section upon insertion therein;
    (3) a third section connected to the second section comprising a cylindrical section of a diameter less than the largest diameter of the second section; and
    (4) a fourth section connected to the third section comprising a handle.

2. An apparatus adapted for insertion in an orifice provided with an inlet and an outlet for determining the extent of wear of the interior conical section of said orifice comprising:
    (1) a first section comprising a cylindrical section of a diameter less than the diameter of the outlet of the orifice;
    (2) a second section connected to the first section comprising a truncated conical section possessing an angle of taper equal to the angle of the interior conical section of the orifice and of such a diameter as to contact the interior conical section of the orifice in a zone contained therein near the outlet of the orifice;
    (3) a third section connected to the second section comprising a cylindrical section of a diameter less than the largest diameter of the second section; and
    (4) a fourth section connected to the third section comprising a handle.

3. The apparatus of claim 2 wherein the orifice is a fluid nozzle.

4. The apparatus of claim 2 wherein the orifice is a venturi.

* * * * *